(12) United States Patent
Altmann et al.

(10) Patent No.: US 7,874,987 B2
(45) Date of Patent: Jan. 25, 2011

(54) TARGETS AND METHODS FOR ULTRASOUND CATHETER CALIBRATION

(75) Inventors: Andres Claudio Altmann, Haifa (IL); Assaf Govari, Haifa (IL)

(73) Assignee: Biosense Webster, Inc., Diamond Bar, CA (US)

( * ) Notice: Subject to any disclaimer, the term of this patent is extended or adjusted under 35 U.S.C. 154(b) by 1486 days.

(21) Appl. No.: 11/263,066

(22) Filed: Oct. 28, 2005

(65) Prior Publication Data

US 2007/0106156 A1    May 10, 2007

(51) Int. Cl.
*A61B 8/00* (2006.01)
(52) U.S. Cl. ............... 600/443; 600/437; 600/459; 600/424
(58) Field of Classification Search ........... 600/437, 600/443, 459, 424
See application file for complete search history.

(56) References Cited

U.S. PATENT DOCUMENTS

| | | | |
|---|---|---|---|
| 6,138,495 A | 10/2000 | Paltieli et al. | |
| 6,266,551 B1 | 7/2001 | Osadchy et al. | |
| 6,370,411 B1 | 4/2002 | Osadchy et al. | |
| 6,585,561 B2 | 7/2003 | Tokutake et al. | |
| 6,690,963 B2 | 2/2004 | Ben-Haim et al. | |
| 6,716,166 B2 | 4/2004 | Govari | |
| 6,773,402 B2 | 8/2004 | Govari et al. | |
| 2004/0254458 A1 | 12/2004 | Govari | |

FOREIGN PATENT DOCUMENTS

| EP | 1481637 A1 | 12/2004 |
|---|---|---|
| WO | WO 2005084551 A2 | 9/2005 |

OTHER PUBLICATIONS

European Search Report Appln. No. 06255545.3.

*Primary Examiner*—Brian Casler
*Assistant Examiner*—John F Ramirez
(74) *Attorney, Agent, or Firm*—Louis J. Capezzuto

(57) ABSTRACT

A method for calibrating an ultrasound probe includes directing the probe to receive ultrasonic waves reflected from a target that includes one or more linear elements, which are arranged to intersect the beam plane of the probe at respective intersection points. Signals are received from the probe responsively to the reflected ultrasonic waves, and the probe is aligned by modifying at least one of a position and an orientation of the probe responsively to the signals so that the intersection points occur in a desired location in the beam plane.

7 Claims, 4 Drawing Sheets

TARGETS AND METHODS FOR ULTRASOUND CATHETER CALIBRATION

CROSS-REFERENCE TO RELATED APPLICATION

This application is related to U.S. patent application Ser. No. 10/447,940, filed May 29, 2003, and published Dec. 16, 2004, as US 2004/0254458 A1, which is assigned to the assignee of the present patent application and whose disclosure is incorporated herein by reference.

FIELD OF THE INVENTION

The present invention relates generally to ultrasound imaging systems, and specifically to devices and methods for calibration of ultrasound probes.

BACKGROUND OF THE INVENTION

The above-mentioned related application describes apparatus and methods for calibrating a probe having a position sensor and an ultrasonic transducer. The apparatus includes a test fixture, which includes an ultrasonic target disposed therein at a known position. A computer receives a position signal generated by the position sensor while the transducer is in alignment with the ultrasonic target. The computer thus determines the orientation of the probe in a frame of reference of the test fixture and determines calibration data for the probe responsive to the orientation of the probe.

Various methods are known in the art for calibrating position sensors. For example, U.S. Pat. Nos. 6,266,551 and 6,370,411, whose disclosures are incorporated herein by reference, describe methods and apparatus for calibrating a probe comprising a magnetic position sensor. The calibration is used to measure and compensate for variations in the positions, orientations and gains of magnetic sensor coils in the probe. To calibrate the probe, a mechanical jig holds the probe in one or more predetermined positions and orientations, and radiators generate known, substantially uniform magnetic fields in the vicinity of the jig. Signals generated by the coils are analyzed and used to produce calibration data regarding the gains of the coils and deviations of the coils from orthogonality.

Other methods for calibrating ultrasound imagers with position sensors are also known in the art. For example, U.S. Pat. No. 6,138,495, whose disclosure is incorporated herein by reference, describes a method and apparatus for calibrating a position measuring component on an imaging or scanning transducer with respect to the scanning plane. Calibrations are performed by using a calibrating device including an additional position measuring component, such that during the calibration process, the relative position of between these position measuring components can be calculated. Calibrations are also performed by viewing targets in the scanning plane that are at a known position with respect to the additional position measuring component.

As another example, U.S. Pat. No. 6,585,561, whose disclosure is incorporated herein by reference, describes a calibration unit for calibrating an ultrasound head. The calibration unit is configured to receive the ultrasound head in a known position and orientation with respect to a reference portion of the calibration unit. The calibration unit allows the calibration of a coordinate system of markers associated with the ultrasound device. Echoes received from the reference portion can be used to calibrate, for example, an offset between the ultrasound head and the reference portion. The calibration unit is preferably formed of a material in which the sound velocity is known, such as a suitable plastic with a hole having a diameter to receive the ultrasound device. During calibration, echoes are received from the interface of the bottom of the calibration unit and the surrounding medium, which is preferably air. The echo can be used to calculate an offset from the ultrasound device head to the interface.

SUMMARY OF THE INVENTION

Embodiments of the present invention provide improved apparatus and methods for calibrating the position and orientation of an ultrasound imaging device with respect to a probe containing the device. These embodiments permit the tilt and offset of the imaging device to be determined accurately relative to the body of the probe.

In some embodiments of the present invention, the probe comprises a position sensor, such as a magnetic position sensor. The determination of tilt and offset of the imaging device are combined with calibration of the position sensor in order to calibrate the position and orientation of the ultrasound beam plane relative to the coordinate frame of the position sensor. Ultrasound images captured by the probe may then be precisely registered with the fixed, three-dimensional frame of reference that is provided by the position sensing system.

There is therefore provided, in accordance with an embodiment of the present invention, a method for calibrating an ultrasound probe having a beam plane, the method including:

directing the probe to receive ultrasonic waves reflected from a target including one or more linear elements, which are arranged to intersect the beam plane at respective intersection points;

receiving signals from the probe responsively to the reflected ultrasonic waves; and aligning the probe by modifying at least one of a position and an orientation of the probe responsively to the signals so that the intersection points occur in a desired location in the beam plane.

In some embodiments, aligning the probe includes forming, using the signals, an ultrasound image in which the intersection points of the linear elements appear as one or more dots, and modifying at least one of the position and the orientation of the probe responsively to the dots appearing in the image. In one embodiment, the one or more linear elements include a plurality of linear elements, and modifying the at least one of the position and the orientation of the probe includes modifying the orientation of the probe responsively to a distance between the dots in the image. Typically, the linear elements cross at a crossing point, and modifying the orientation includes rotating the probe so that the one or more dots converge to a single dot corresponding to the crossing point.

In another embodiment, the one or more linear elements include at least one linear element that is slanted relative to the plane of the image, and modifying the at least one of the position and the orientation of the probe includes modifying the orientation of the probe responsively to a distance between an origin of the image and a dot in the image corresponding to the at least one linear element.

In some embodiments, the probe includes a position sensor, and the method includes calibrating the position sensor so as to determine calibration factors for use in computing coordinates applicable to ultrasound images formed by the probe based on readings of the position sensor. Optionally, the method includes verifying the calibration factors by the steps of calculating, using the calibration factors, a first displacement between the probe and a feature appearing in one of the images formed by the probe while the probe is in a first position; moving the probe to a second position in which the probe contacts the feature; determining, using the position sensor, a second displacement between the first and second positions of the probe; and comparing the first and second displacements.

There is also provided, in accordance with an embodiment of the present invention, a method for calibrating an ultrasound probe having a beam plane, the method including:

directing the probe to receive ultrasonic waves reflected from a target including an object that intersects the beam plane and is slanted relative to the plane;

receiving signals from the probe responsively to the reflected ultrasonic waves; and aligning the probe by modifying at least one of a position and an orientation of the probe responsively to the signals so that the object intersects the beam plane in a desired location.

In some embodiments, aligning the probe includes forming, using the signals, an ultrasound image in which the object appears as a feature, and modifying at least one of the position and the orientation of the probe responsively to the feature appearing in the image. Typically, modifying the at least one of the position and the orientation of the probe includes modifying the orientation of the probe responsively to a distance between the feature and an origin of the image. In one embodiment, the object includes a linear element, and the feature includes a dot. In another embodiment, the object includes a planar element, and the feature includes a line.

There is also provided, in accordance with an embodiment of the present invention, apparatus for calibrating an ultrasound probe having a beam plane, the apparatus including:

a console, which is adapted to be coupled to the probe so as to receive signals from the probe responsively to ultrasonic waves incident upon the probe; and an alignment fixture, including:

a target, including one or more linear elements that intersect the beam plane at respective intersection points; and a mount, which is adapted to hold the probe while permitting at least one of a position and an orientation of the probe to be modified, responsively to the signals received by the console, so that the intersection points occur in a desired location in the beam plane.

There is additionally provided, in accordance with an embodiment of the present invention, apparatus for calibrating an ultrasound probe having a beam plane, the apparatus including:

a console, which is adapted to be coupled to the probe so as to receive signals from the probe responsively to ultrasonic waves incident upon the probe; and an alignment fixture, including:

a target, including an object that intersects the beam plane and is slanted relative to the plane; and a mount, which is adapted to hold the probe while permitting at least one of a position and an orientation of the probe to be modified, responsively to the signals received by the console, so that the object intersects the beam plane in a desired location.

The present invention will be more fully understood from the following detailed description of the embodiments thereof, taken together with the drawings in which:

DETAILED DESCRIPTION OF EMBODIMENTS

Figure 1:
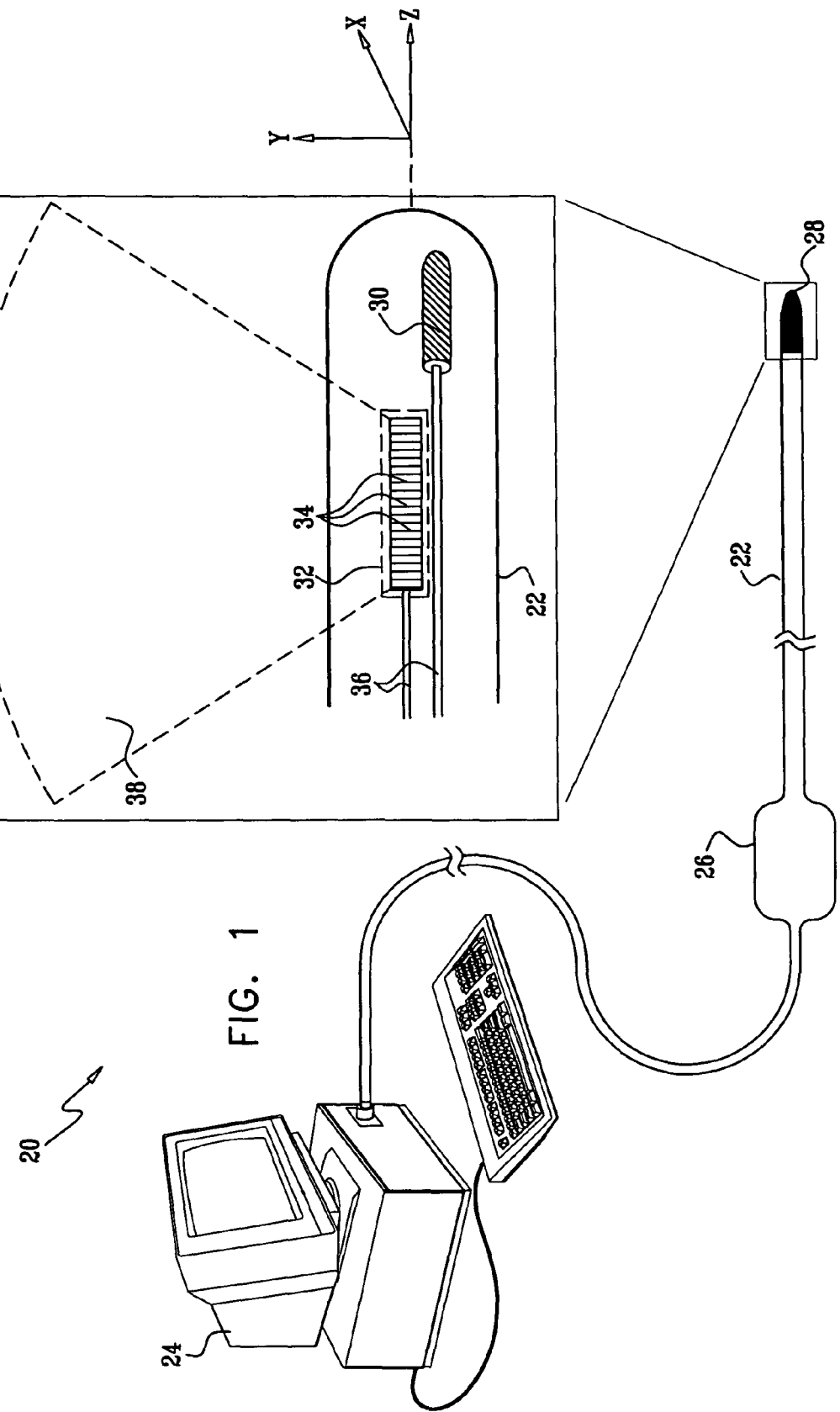
FIG. 1 is a schematic, pictorial illustration of a catheter-based system for ultrasonic imaging, in accordance with an embodiment of the present invention.

FIG. 1 is a schematic, pictorial illustration of an ultrasonic imaging system 20 comprising an elongate probe, such as a catheter 22, for insertion into the body of a patient, in accordance with an embodiment of the present invention. System 20 comprises a console 24, which typically comprises a computer with suitable signal processing and user interface circuits. This console receives and processes signals from catheter 22, as described hereinbelow. Typically, the console enables a user to observe and regulate the functions of catheter 20 and displays images that are formed using the catheter. Catheter 20 typically includes a handle 26 for controlling operation of the catheter by the user. The handle or a connector coupling the catheter to console 24 may comprise a microcircuit for storing calibration data, as described in the above-mentioned U.S. Pat. No. 6,266,551, for example.

A distal end 28 of catheter 22 comprises an ultrasound imaging device 32, which is used to produce ultrasound images of the inside of the body. An enlarged, cross-sectional view of distal end 28 is shown in the inset in FIG. 1. Ultrasound imaging device 32 typically comprises a phased array of transducers 34, which is operated, as is known in the art, so as to create a two-dimensional image "fan" 38 in the plane of the scanning ultrasonic beam (referred to herein as the "beam plane"), which contains the longitudinal axis of the catheter (identified as the Z-axis in the figures). The transducers receive ultrasonic waves that are reflected from objects in the beam plane and output signals in response to the reflected waves. Typically, these signals are processed by console 24 in order form and display ultrasound images. Alternatively or additionally, ultrasound transducers 34 may be used for other diagnostic purposes, such as Doppler measurements, or for therapeutic uses.

Distal end 28 of catheter 22 further comprises a position sensor 30, which generates signals that indicate the position and orientation of the catheter within the body. Based on these position signals, console 24 determines the location and orientation of each fan image captured by imaging device 32. The console is thus able to determine the coordinates of objects appearing in the fan image, as well as to combine multiple images captured at different catheter positions.

Position sensor 30 is typically adjacent to imaging device 32 in a fixed positional and orientational relationship. In some embodiments, the position sensor comprises one or more coils, which produce signals in response to a magnetic field generated by a field generator outside the patient's body. The signals are analyzed by console 24 in order to determine position and orientation coordinates of distal end 28. This sort of magnetic position sensing is described in detail, for example, in the above-mentioned U.S. Pat. No. 6,266,551. Other exemplary systems that combine ultrasonic imaging with magnetic position sensing are described in U.S. Pat. Nos. 6,690,963, 6,716,166 and 6,773,402, whose disclosures are incorporated herein by reference.

Alternatively, catheter 22 may comprise any other suitable type of position sensor known in the art. For example, position sensor 30 may comprise other types of field sensing devices, such as a Hall Effect sensor. Alternatively, sensor 30 may generate magnetic fields, which are detected by sensing antennas outside the body. Further alternatively, position sensor 30 may operate by measuring impedance of the body to electrical signals or by transmitting or receiving ultrasonic position signals. The principles of the present invention are applicable to substantially any position sensing technology that can be implemented in a medical probe.

As shown in FIG. 1, due to physical constraints in the construction of catheter 22, position sensor 30 and ultrasound image device 32 are both located in catheter 22 at certain respective distances from the distal tip of the catheter. The actual position and orientation of fan 38 is computed by taking into account the distance between the position sensor and the ultrasound imaging device. It has been found empirically that because of deviations in the process of manufacturing catheter 22, this distance typically varies from one catheter to another. Furthermore, the axes of the position sensor and of the ultrasonic transducer array in imaging device 32 may not be precisely aligned with the Z-axis or with one another other, thereby introducing additional variation in determining the orientation of fan 38. These and other sources of alignment variation are described in greater detail in the above-mentioned Patent Application Publication US 2004/0254458 A1. If not corrected, the alignment variation will cause errors in determining the position coordinates of objects appearing in image fan 38.

Figure 2:
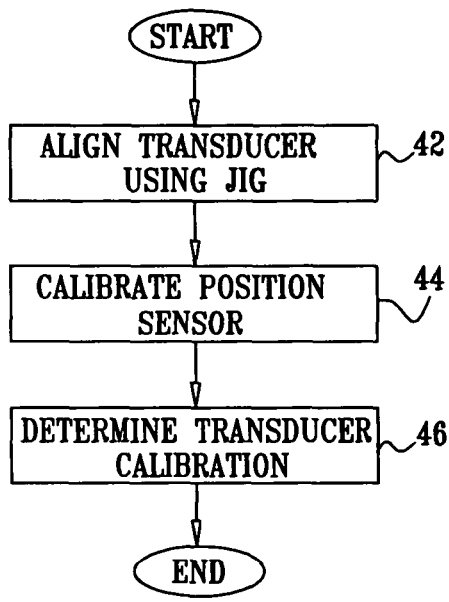
FIG. 2 is a flow chart that schematically illustrates a method for calibrating an ultrasound probe, in accordance with an embodiment of the present invention.

FIG. 2 is a flow chart that schematically illustrates a method for calibrating an ultrasonic probe, such as catheter 22, in order to correct for alignment variations, in accordance with an embodiment of the present invention. Initially, the catheter is mechanically aligned in a fixture (also referred to herein as a jig), at a transducer alignment step 42. Exemplary fixtures that may be used for this purpose are shown in the figures that follow. The purpose of this step is to manipulate the position and orientation of distal end 28 in a controlled manner so as to bring ultrasound imaging device 32 into alignment with a fixed external coordinate system. In other words, the catheter is translated and rotated in the fixture until fan 38 is in the desired location and orientation. Typically, the catheter is manipulated in step 42 so that fan 38 is aligned in the Y-Z plane (with respect to the coordinate system shown in FIG. 1) and is centered longitudinally at the origin of the XYZ coordinates.

Once the catheter has been properly positioned and oriented at step 42, position sensor 30 is calibrated, at a sensor calibration step 44. During step 44, the catheter is fixed relative to the fixture in the aligned position and orientation that were determined at step 42. In embodiments in which sensor 30 is a magnetic position sensor, magnetic fields of known magnitude and direction are applied to the catheter, and the signals generated by the sensor are measured in order to compute calibration factors. This step is described in detail in the above-mentioned U.S. Pat. No. 6,266,551 and Patent Application Publication US 2004/0254458 A1, for example. During step 44, catheter 22 is typically fixed in the aligned position and orientation that were determined at step 42. Alternatively, the catheter may be shifted and/or rotated by a known amount.

Alternatively, the order of steps 42 and 44 may be reversed. In other words, position sensor 30 may first be calibrated at step 44. Then, when the catheter is aligned in the fixture at the conclusion of step 42, the location and orientation coordinates of catheter 22 are read out using position sensor 30.

Based on the results of steps 42 and 44 (in whichever order the steps are carried out), calibration factors are determined for imaging device 32, at a transducer calibration step 46. The calibration factors indicate the actual location and orientation of fan 38 as a function of the magnetic field signals generated by position sensor 30. These calibration factors are used subsequently by console 24 in determining the correct position and orientation of fan 38, based on position readings provided, by sensor 30, and in finding the correct position and orientation coordinates of objects seen in the fan image. Optionally, the calibration factors may be verified, as described below with reference to FIGS. 6A and 6B, for example.

Figure 3:
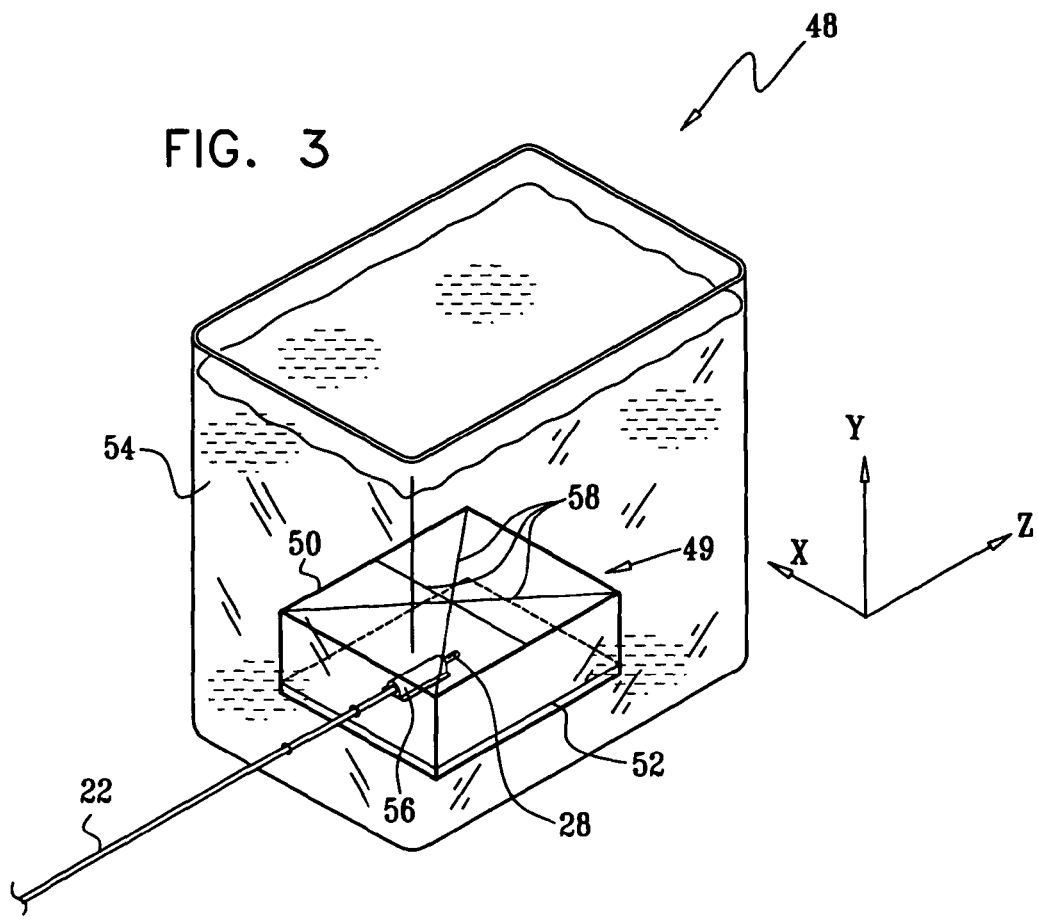
FIG. 3 is a schematic, pictorial illustration of a system for aligning an ultrasound probe, in accordance with an embodiment of the present invention.

FIG. 3 is a schematic, pictorial illustration of a system 48 for aligning catheter 22 at step 42, in accordance with an embodiment of the present invention. System 48 comprises an alignment fixture 49, which comprises a base 52 and an alignment target 50 made up of linear elements, such as crosshairs 58. Although three crosshairs are shown in FIG. 3, the target may alternatively comprise smaller or greater numbers of crosshairs. Crosshairs 58 may comprise metal wires or any other suitable ultrasound-reflecting material. Catheter 22 is held in a mount 56 on base 52 so that distal end 28 of the catheter is positioned beneath the central crossing point of wires 58 in the alignment target. Fixture 49 typically comprises alignment controls (not shown), which permit catheter 22 to be rotated and translated so as to align imaging device 32 with the target. During alignment, fixture 49 and catheter 22 may be immersed in a bath 54, since ultrasound waves generally travel better in fluid (such as water) than they do in air.

Figure 4:
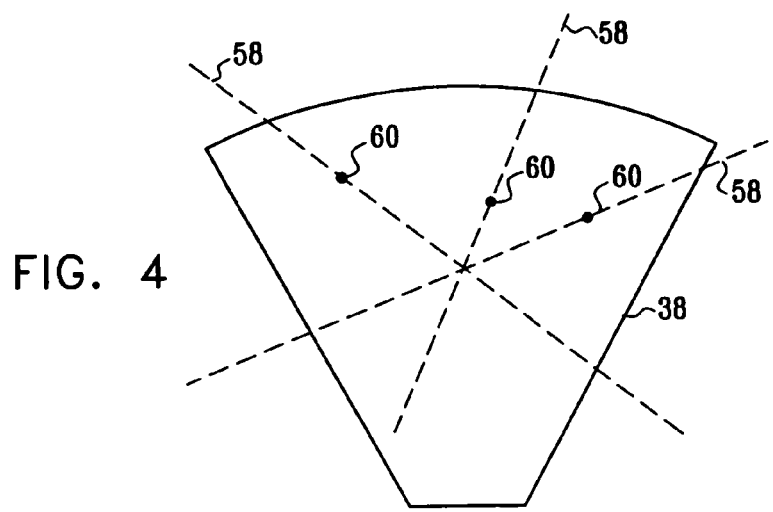
FIG. 4 is a schematic representation of an ultrasound image formed by a probe in the system of FIG. 3, in accordance with an embodiment of the present invention.

FIG. 4 is a schematic representation of image fan 38 that is produced by catheter 22 in fixture 49, in accordance with an embodiment of the present invention. Each of crosshairs 58 intersects the plane of image fan 38 at one respective point, so that the crosshairs appear as dots 60 in the image. When imaging device 32 is perfectly aligned with target 50, the plane of fan 38 intersects the crossing point of the crosshairs, so that dots 60 converge to a single dot in the image. In the example shown in FIG. 4, however, dots 60 are spread apart, indicating that catheter 22 is rotationally offset about the Z-axis relative to target 50. Thus, in order to align catheter 22 with fixture 49, the catheter is rotated about the Z-axis until the three dots converge. Typically, to align the catheter, an operator of system 20 manipulates the catheter in mount 56 while observing the fan image on the display of console 24.

Alternatively or additionally, the alignment at step 42 may be carried out using signal processing by console 24. For example, the console may analyze the amplitudes, envelopes and/or temporal features of the signals received from imaging device 32 in order to determine whether catheter 22 is properly aligned and, if not, how the catheter should be adjusted for proper alignment. The actual alignment correction may then be performed manually by a human operator or at least semi-automatically under closed-loop computer control. Although the embodiments described herein refer mainly to the use of images as alignment aids, the principles of the present invention may equivalently be implemented by means of this sort of signal processing, without necessarily forming ultrasound images during alignment.

In addition, a line drawn through dots 60 in FIG. 4 is skewed relative to the horizontal, because crosshairs 58 intersect fan 38 at different distances from imaging device 32. In addition, the distances between the two side dots and the central dot are not equal. The skew and unequal dot distances indicate that the axis of the imaging device is tilted relative to the Z-axis. To correct the skew, the tilt of catheter 22 in mount 56 is adjusted until dots 60 form a straight, horizontal line and so that the distances between the dots are equal. In this situation, the imaging device is known to be parallel to the Z-axis, and may then be rotated until dots 60 converge, at which point the angular alignment of the catheter is complete.

The displacement of distal end 28 of the catheter may also be adjusted in the X, Y, and Z-directions so that the dot corresponding to the crossing point of the crosshairs (when dots 60 have converged) is located on the center line of fan 38, at a predefined distance from the origin of the fan. At this point, imaging device 32 is known to be centered directly below the crossing point of crosshairs 58, at the desired distance from target 50.

When adjustment of the position and orientation of catheter 22 in fixture 49 has been completed, the catheter is fixed in place in mount 56 and is kept clamped in this position and orientation during calibration of position sensor 30 at step 44 (FIG. 2). This step may be carried out with system 48 in situ, i.e., without removing the catheter from bath 54. In other words, assuming sensor 30 to be a magnetic position sensor, for example, system 48 may be located within the magnetic fields of calibration field generator coils, which are actuated so as to calibrate sensor 30 without moving catheter 22 at all following step 42. This approach, which is described in the above-mentioned Patent Application Publication US 2004/0254458 A1, is advantageous in terms of convenience and accuracy of calibration, but requires a large and complex calibration system.

Alternatively, in preparation for step 44, fixture 49 may be removed from bath 54 and moved to a separate position sensor calibration setup, such as that shown in the above-mentioned U.S. Pat. No. 6,266,551. This latter setup is typically configured to accept base 52 so that the X-Y-Z axes of the position sensor calibration setup are aligned exactly with those defined by target 50 at step 42. Thus, the position and orientation of imaging device 32 are aligned with the axes of the position sensor calibration setup before the position sensor calibration factors are determined.

Figure 5A:
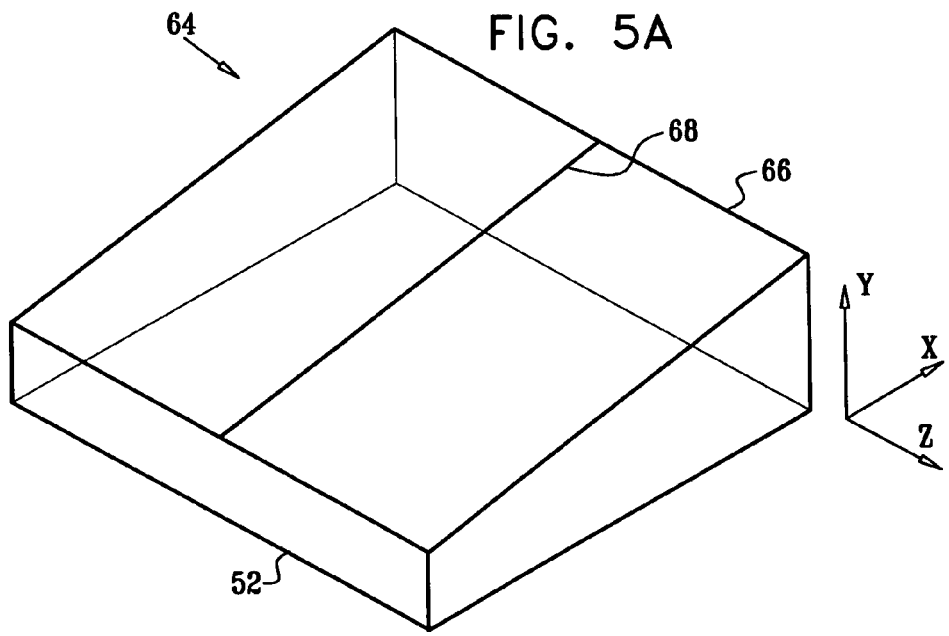
FIG. 5A is a schematic, pictorial illustration of a fixture for calibrating an ultrasound probe, in accordance with another embodiment of the present invention.
Figure 5B:
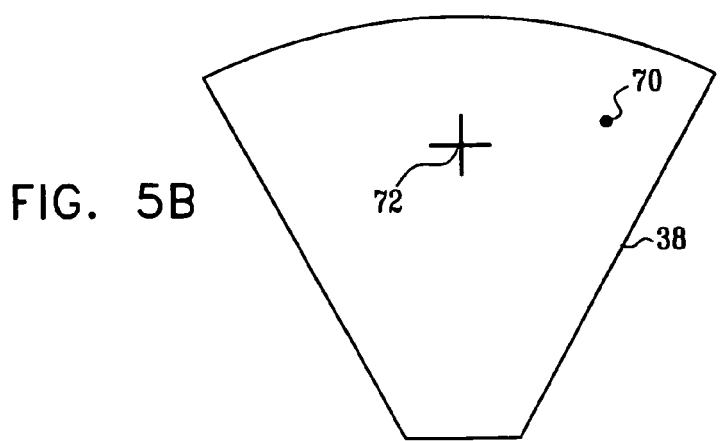
FIG. 5B is a schematic representation of an ultrasound image formed by a probe in the fixture of FIG. 5A, in accordance with an embodiment of the present invention.

Reference is now made to FIGS. 5A and 5B, which schematically illustrate another fixture and method that may be used for alignment of catheter 22 at step 42, in accordance with an alternative embodiment of the present invention. FIG. 5A is a schematic, pictorial illustration of an alignment fixture 64, while FIG. 5B is a schematic representation of image fan 38 that is produced using fixture 64.

In this embodiment, fixture 64 comprises a target 66, having a single crosshair 68, which is slanted relative to the X-Z plane. The crosshair appears as a dot 70 in fan 38. The distance of the dot from the origin of the fan varies depending upon the point at which crosshair 68 intersects the fan, and thus is indicative of the rotation of imaging device 32 relative to the Z-axis. To align the imaging device, catheter 22 is rotated and translated relative to base 52 until dot 70 is located on a central point 72.

As another alternative, not shown in the figures, the alignment target used at step 42 comprises a slanted planar element, such as a slanted surface. In this case, the intersection of fan 38 with the surface will appear as a line running across the fan image. The catheter is aligned until this line in the image is properly oriented at the desired distance from the origin of the fan.

Figure 6A:
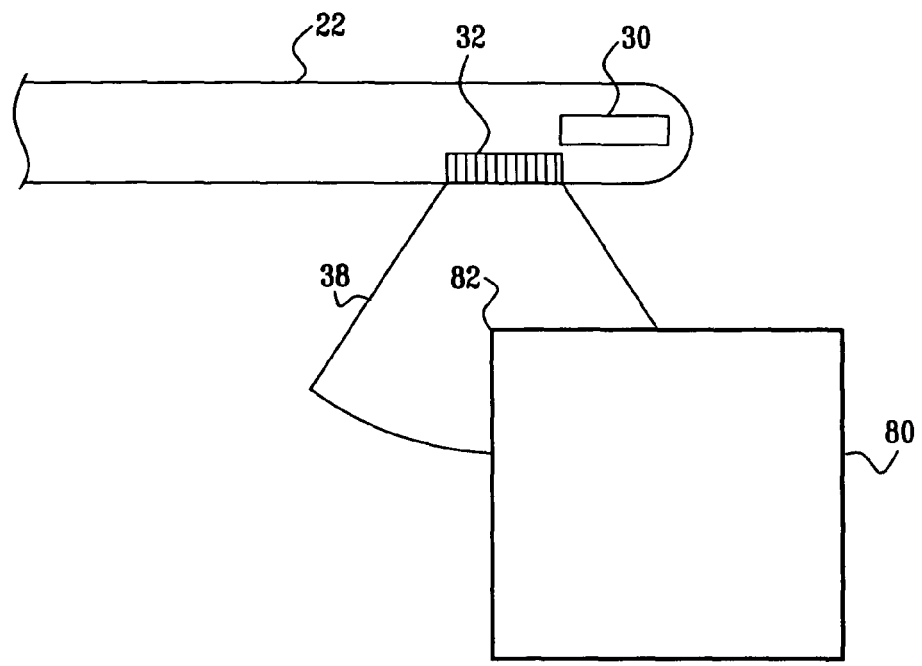
FIGS. 6A and 6B are schematic side views of a ultrasound probe, illustrating successive stages in a procedure for verifying proper calibration of the probe, in accordance with an embodiment of the present invention.
Figure 6B:
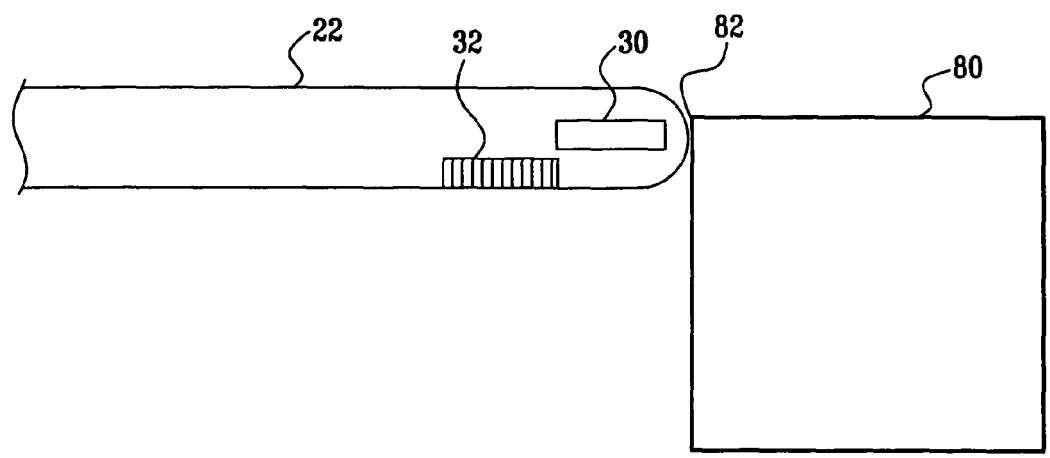

FIGS. 6A and 6B are schematic side views of catheter 22 and of a target 80, illustrating a procedure for verifying the calibration of imaging device 32, in accordance with an embodiment of the present invention. After the calibration procedure of FIG. 2 has been completed, system 20 can accurately determine three-dimensional coordinates of any feature seen in fan images produced by catheter 22. To test the accuracy of the calibration, catheter 22 is used to form an image of target 80, as shown in FIG. 6A. The target may be an ultrasound phantom, for example. The coordinates of the catheter are determined using the readings provided by position sensor 30. A feature, such as a corner 82 of the phantom, is identified in the ultrasound image, and console 24 determines the displacement of the corner in the image relative to the origin of fan 38.

Next, as shown in FIG. 6B, catheter 22 is moved so that it touches corner 82. The displacement of the catheter in this location is computed relative to the location of FIG. 6A, using the coordinate readings provided by position sensor 30. This coordinate displacement is compared to the previously-determined image feature displacement of the corner relative to the origin of the fan. If system 20 is calibrated correctly, the two displacement values will be equal. Other comparative tests of image feature displacement relative to coordinate sensing displacement may similarly be used for this purpose.

Although the embodiments described above make reference specifically to catheter 22, the principles of the present invention are equally applicable to other types of ultrasound probes, including both invasive probes and probes used outside the body. It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A method for calibrating an ultrasound probe having a beam plane, the method comprising:
    directing the probe to receive ultrasonic waves reflected from a target comprising one or more linear elements, arranged to intersect the beam plane at respective intersection points;
    receiving signals from the probe responsive to the reflected ultrasonic waves; and
    aligning the probe by modifying at least one of a position and an orientation of the probe responsively to the signals so that the intersection points occur in a desired location in the beam plane, said step of aligning the probe comprising:
        forming, using the signals, an ultrasound image in which the intersection points of the linear elements appear as one or more dots; and
        modifying at least one of the position and the orientation of the probe responsive to the dots appearing in the image;
    wherein the one or more linear elements comprise a plurality of linear elements, and modifying the at least one of the position and the orientation of the probe comprises modifying the orientation of the probe responsive to a distance between the dots in the image, and wherein the linear elements cross at a crossing point, and modifying the orientation comprises rotating the probe so that the one or more dots converge to a single dot corresponding to the crossing point.

2. The method according to claim 1, wherein the one or more linear elements comprise at least one linear element that is slanted relative to the plane of the image, and wherein modifying the at least one of the position and the orientation of the probe comprises modifying the orientation of the probe responsively to a distance between an origin of the image and a dot in the image corresponding to the at least one linear element.

3. The method according to claim 1, wherein the probe includes a position sensor, and wherein the method comprises calibrating the position sensor so as to determine calibration factors for use in computing coordinates applicable to ultrasound images formed by the probe based on readings of the position sensor.

4. The method according to claim 3, and comprising verifying the calibration factors by the steps of:

calculating, using the calibration factors, a first displacement between the probe and a feature appearing in one of the images formed by the probe while the probe is in a first position;

moving the probe to a second position in which the probe contacts the feature;

determining, using the position sensor, a second displacement between the first and second positions of the probe; and comparing the first and second displacements.

5. Apparatus for calibrating an ultrasound probe having a beam plane, the apparatus comprising:

a console, which is adapted to be coupled to the probe so as to receive signals from the probe responsively to ultrasonic waves incident upon the probe; and an alignment fixture, comprising:

a target, comprising one or more linear elements arranged to intersect the beam plane at respective intersection points; and a mount adapted to hold the probe while permitting at least one of a position and an orientation of the probe to be modified, responsive to the signals received by the console, so that the intersection points occur in a desired location in the beam plane, wherein the console is operative to display, based on the signals, an ultrasound image in which the intersection points of the linear elements appear as one or more dots, and the mount is adapted to permit at least one of the position and the orientation of the probe to be modified until the one or more dots appear in a desired location in the image, wherein the one or more linear elements comprises a plurality of linear elements, and the orientation of the probe is modified responsive to a distance between the dots in the image, and wherein the linear elements cross at a crossing point, and the mount permits the probe to be rotated so that the one or more dots converge to a single dot corresponding to the crossing point.

6. The apparatus according to claim 5, wherein the one or more linear elements comprise at least one linear element that is slanted relative to the plane of the image, and wherein the orientation of the probe is modified responsively to a distance between an origin of the image and a dot in the image corresponding to the at least one linear element.

7. The apparatus according to claim 5, wherein the probe includes a position sensor, and wherein the apparatus comprises a position sensor calibration setup, which is adapted to determine calibration factors for use in computing coordinates applicable to ultrasound images formed by the probe based on readings of the position sensor.

* * * * *